(12) United States Patent
Blomqvist et al.

(10) Patent No.: US 11,813,064 B2
(45) Date of Patent: Nov. 14, 2023

(54) APPARATUS AND ELECTRONIC CIRCUITRY FOR SENSING BIOSIGNALS

(71) Applicant: Nokia Technologies Oy, Espoo (FI)

(72) Inventors: Kim Blomqvist, Espoo (FI); Satu Rajala, Kangasala (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 16/136,522

(22) Filed: Sep. 20, 2018

(65) Prior Publication Data

US 2019/0099097 A1 Apr. 4, 2019

(30) Foreign Application Priority Data

Oct. 2, 2017 (EP) .................................... 17194437

(51) Int. Cl.
*A61B 5/11* (2006.01)
*A61B 5/25* (2021.01)
(Continued)

(52) U.S. Cl.
CPC .............. *A61B 5/30* (2021.01); *A61B 5/1102* (2013.01); *A61B 5/113* (2013.01); *A61B 5/25* (2021.01); *A61B 5/291* (2021.01); *A61B 5/6801* (2013.01); *A61B 5/02405* (2013.01); *A61B 5/0531* (2013.01); *A61B 5/0533* (2013.01); *A61B 5/259* (2021.01); *A61B 5/302* (2021.01); *A61B 5/316* (2021.01); *A61B 5/389* (2021.01); *A61B 5/7225* (2013.01); *A61B 2562/0214* (2013.01); *A61B 2562/164* (2013.01)

(58) Field of Classification Search
CPC . A61B 5/04004; A61B 5/0408; A61B 5/0478; A61B 5/113; A61B 5/6801; A61B 5/1102; A61B 5/04087; A61B 2562/0214; A61B 5/7225; A61B 5/0531; A61B 5/04284; A61B 2562/164; A61B 5/02405; A61B 5/04012; A61B 5/0488; A61B 5/0533
See application file for complete search history.

(56) References Cited

U.S. PATENT DOCUMENTS 4,742,831 A * 5/1988 Silvian .................. A61B 5/301
                                                              600/523
9,445,740 B1 * 9/2016 Crone .................. A61B 5/6802
(Continued)

OTHER PUBLICATIONS

Noh et al. "Ferroelectret film-based patch-type sensor for continuous blood pressure monitoring" Electronics Let, vol. 50, No. 3, Jan. 30, 2014 (Jan. 30, 2014), pp. 143-144 (Year: 2014).*
(Continued)

*Primary Examiner* — Nathan J Jenness
(74) *Attorney, Agent, or Firm* — Harrington & Smith

(57) ABSTRACT

An apparatus and electronic circuitry wherein the apparatus includes a first electrode arranged to enable an output indicative of a bioelectrical signal to be provided; a second electrode; and a deformable material positioned between the first electrode and the second electrode wherein the deformable material is positioned within the apparatus such that deformation of the deformable material causes a change in charge distribution across the first electrode and second electrode to enable an output indicative of a biomechanical signal to be provided by the apparatus.

6 Claims, 3 Drawing Sheets

Figure 1:
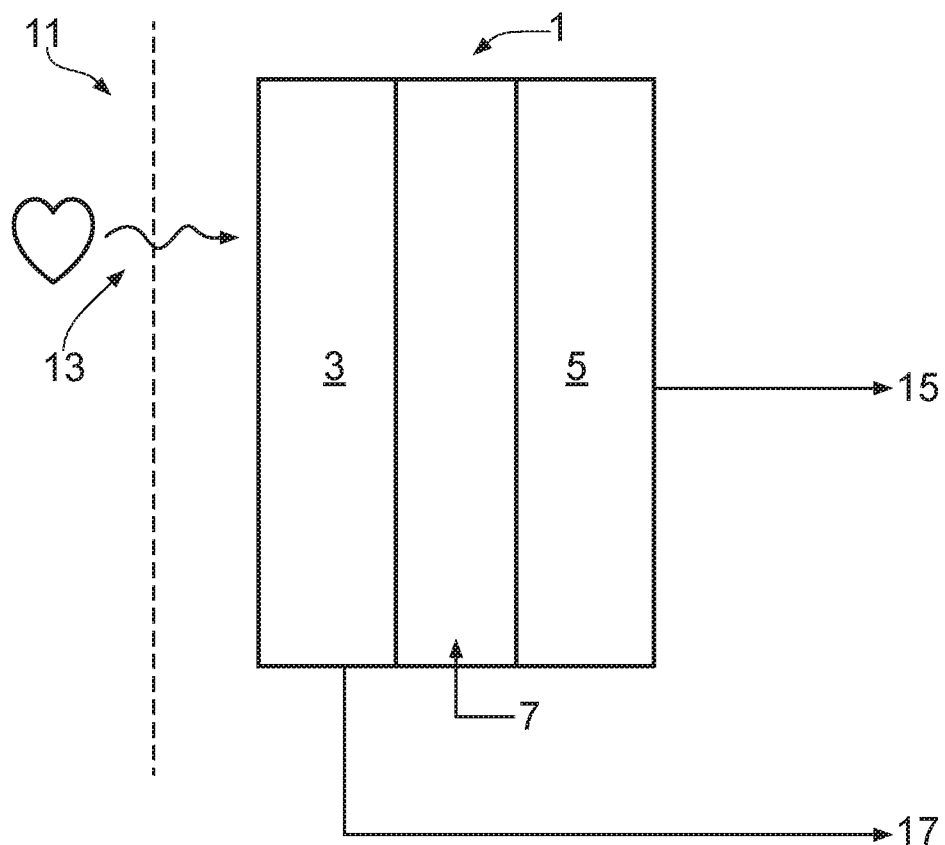

(51) Int. Cl.
  *A61B 5/30*      (2021.01)
  *A61B 5/291*     (2021.01)
  *A61B 5/113*     (2006.01)
  *A61B 5/00*      (2006.01)
  *A61B 5/0531*    (2021.01)
  *A61B 5/259*     (2021.01)
  *A61B 5/302*     (2021.01)
  *A61B 5/316*     (2021.01)
  *A61B 5/389*     (2021.01)
  *A61B 5/024*     (2006.01)
  *A61B 5/0533*    (2021.01)

(56) References Cited

U.S. PATENT DOCUMENTS

| | | | |
|---|---|---|---|
| 2003/0120329 A1* | 6/2003 | Getsla | A61N 1/0452 607/149 |
| 2008/0194975 A1* | 8/2008 | MacQuarrie | A61B 5/1102 600/483 |
| 2008/0269625 A1* | 10/2008 | Halperin | A61B 5/6892 600/508 |
| 2010/0137726 A1* | 6/2010 | Matsumura | A61B 5/0408 600/509 |
| 2013/0184600 A1* | 7/2013 | Tan | A61B 5/721 600/518 |
| 2014/0100432 A1* | 4/2014 | Golda | A61B 5/0295 600/301 |
| 2014/0200054 A1* | 7/2014 | Fraden | H04M 1/72575 455/575.8 |
| 2016/0051156 A1* | 2/2016 | Kim | A61B 5/4866 600/513 |

OTHER PUBLICATIONS

Wu et al. "Assessment of Biofeedback Training for Emotion Management Through Wearable Textile Physiological Monitoring System" IEEE Sensors Journal, vol. 15, No. 12, Dec. 1, 2015 (Dec. 1, 2015), pp. 7087-7095 (Year: 2015).*

Gong et al. "Electric Field Sensors Based on MEMS Technology" Journal of Electronics vol. 22 No. 4 pp. 443-448 (Year: 2015).*

Baranov, Pavel & Tsimbalist, E. & Borikov, Valeriy & Pisarenko, J.. (2016). Increasing common-mode rejection ratio based on the voltage follower. 1-3. 10.1109/SIBCON.2016.7491843. (Year: 2016).* https://en.wikipedia.org/wiki/Ground_(electricity) accessed Oct. 8, 2021, backdated to Aug. 24, 2017 using https://web.archive.org/web/20170824043516/https://en.wikipedia.org/wiki/Ground_%28electricity%29 (Year: 2017).*

Baek, Hyan Jae et al., « A Smart Health Monitoring Chair for Nonintrusive Measurement of Biological Signals, IEEE Transactions on Information Technology in Biomedicine, vol. 16, No. 1, Jan. 2012, pp. 150-158.

* cited by examiner

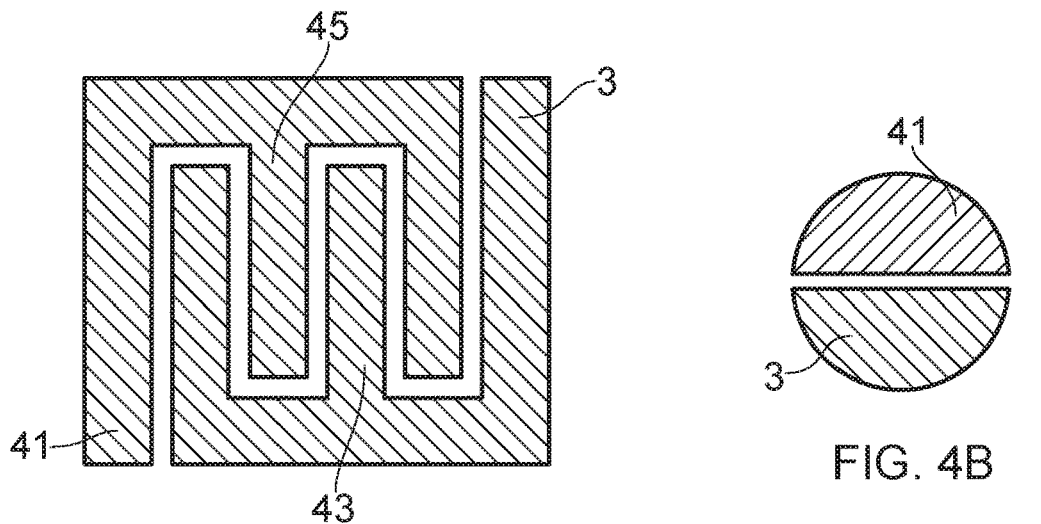
FIG. 4A
FIG. 4B
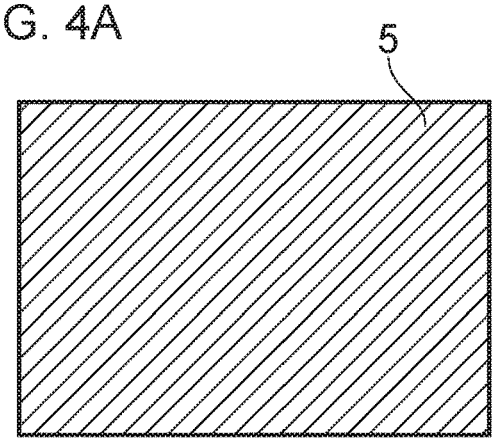
FIG. 4C
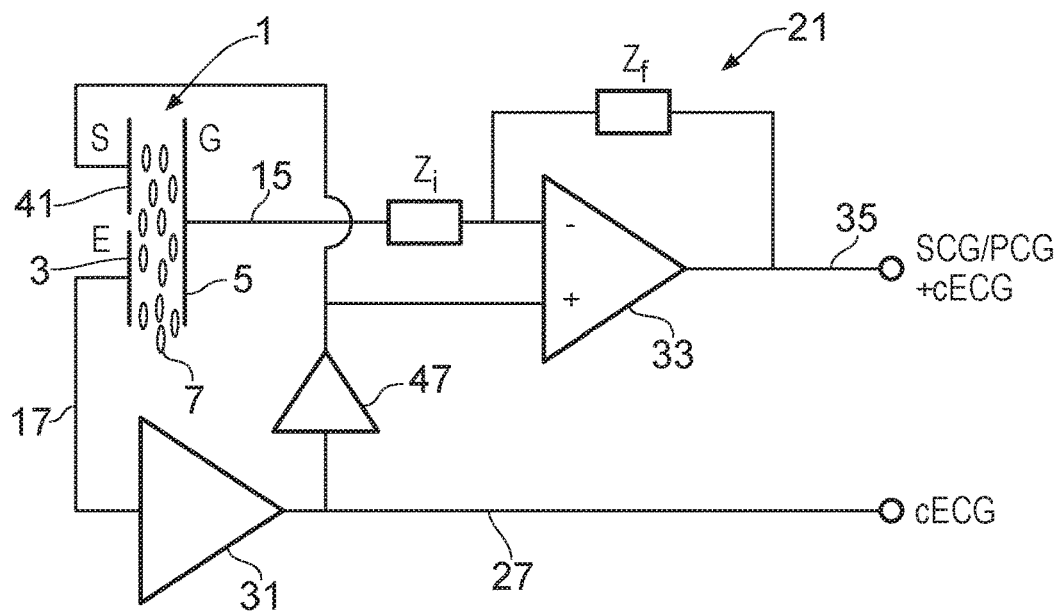
FIG. 4D

APPARATUS AND ELECTRONIC CIRCUITRY FOR SENSING BIOSIGNALS

TECHNOLOGICAL FIELD

Examples of the disclosure relate to apparatus and electronic circuitry for sensing biosignals. In particular they relate to apparatus and electronic circuitry for sensing both bioelectric and biomechanical signals.

BACKGROUND

Measurements of biosignals can be used to obtain information about a subject's health and/or physical state. A subject produces different types of biosignals such as bioelectrical signals and biomechanical signals. Bioelectrical signals may comprise signals which relate to changes in the electrical potential within the subject's body and biomechanical signals may comprise signals which relate to movement of the subject's body such as vibrations caused by the subject's heartbeat.

It is useful to be able to obtain information from different types of biosignals such as bioelectric and biomechanical signals. This can provide more information about the subject and can ensure that more accurate information is obtained. Therefore it is useful to have an apparatus and electronic circuitry which can obtain such information.

BRIEF SUMMARY

According to various, but not necessarily all, examples of the disclosure, there is provided an apparatus comprising: a first electrode arranged to enable an output indicative of a bioelectrical signal to be provided; a second electrode; and a deformable material positioned between the first electrode and the second electrode wherein the deformable material is positioned within the apparatus such that deformation of the deformable material causes a change in charge distribution across the first electrode and second electrode in response to deformation of the deformable material to enable an output indicative of a biomechanical signal to be provided by the apparatus.

The deformable material may comprise at least one of; ferroelectret film, piezoelectric film.

The second electrode may provide an electrical guard for the first electrode.

The second electrode may provide an output indicative of the biomechanical signal and a guard voltage of the first electrode.

The apparatus may be arranged to be coupled to circuitry arranged to measure the bioelectric signal and the biomechanical signal.

The apparatus may be arranged to be coupled to circuitry arranged to separate the biomechanical signal from the bioelectric signal.

The bioelectrical signal may comprise at least one of electrocardiogram signal, electroencephalogram signal, electromyogram signal, electrooculogram signal, electrogastrogram signal, galvanic skin potential.

The biomechanical signal may comprise at least one of ballistocardiogram signal, seismocardiogram signal, phonocardiogram signal.

The apparatus may be arranged to be positioned on the body of a subject.

The first electrode may be arranged to be positioned between the second electrode and the subject's body.

The first electrode may comprise one or more discontinuities.

According to various, but not necessarily all, examples of the disclosure there may be provided electronic circuitry comprising: means for receiving a first input signal from a sensing apparatus; means for receiving a second input signal from the sensing apparatus; means for processing the first input signal and the second input signal so as to enable a biomechanical signal to be separated from a bioelectrical signal; wherein the means for processing the first input signal and the second input signal is coupled to a first output arranged to provide an output indicative of the bioelectric signal coupled to a second output arranged to provide an output indicative of the biomechanical signal.

The means for processing may comprise circuit components arranged to separate the biomechanical signal from the bioelectrical signal.

The electronic circuit may be arranged so that the first input signal is received from a first electrode of the sensing apparatus.

The means for receiving a first input signal may be coupled to a non-inverting amplifier.

The electronic circuit may be arranged so that the second input signal is received from a second electrode of the sensing apparatus, wherein the second electrode is coupled to the first electrode.

The electronic circuit may be arranged so that the second electrode is biased to the voltage of the first electrode.

The means for receiving a second input signal may be coupled to a charge amplifier.

The output of the non-inverting amplifier may be provided as a reference input to the charge amplifier.

The electronic circuitry may comprise a difference amplifier arranged to remove a reference voltage from the biomechanical signal.

According to various, but not necessarily all, examples of the disclosure there may be provided electronic circuitry comprising: a first input arranged to receive a first input signal from a sensing apparatus; a second input arranged to receive a second input signal from the sensing apparatus; processing circuitry arranged to process the first input signal and the second input signal so as to enable a biomechanical signal to be separated from a bioelectrical signal; wherein the processing circuitry is coupled to a first output arranged to provide an output indicative of the bioelectric signal coupled to a second output arranged to provide an output indicative of the biomechanical signal.

BRIEF DESCRIPTION

Figure 2:
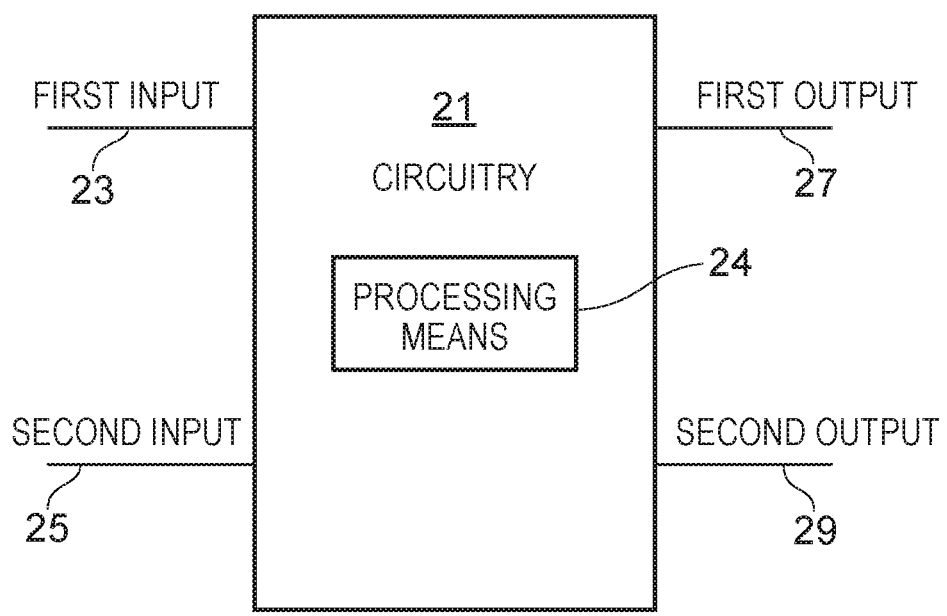
Figure 3:
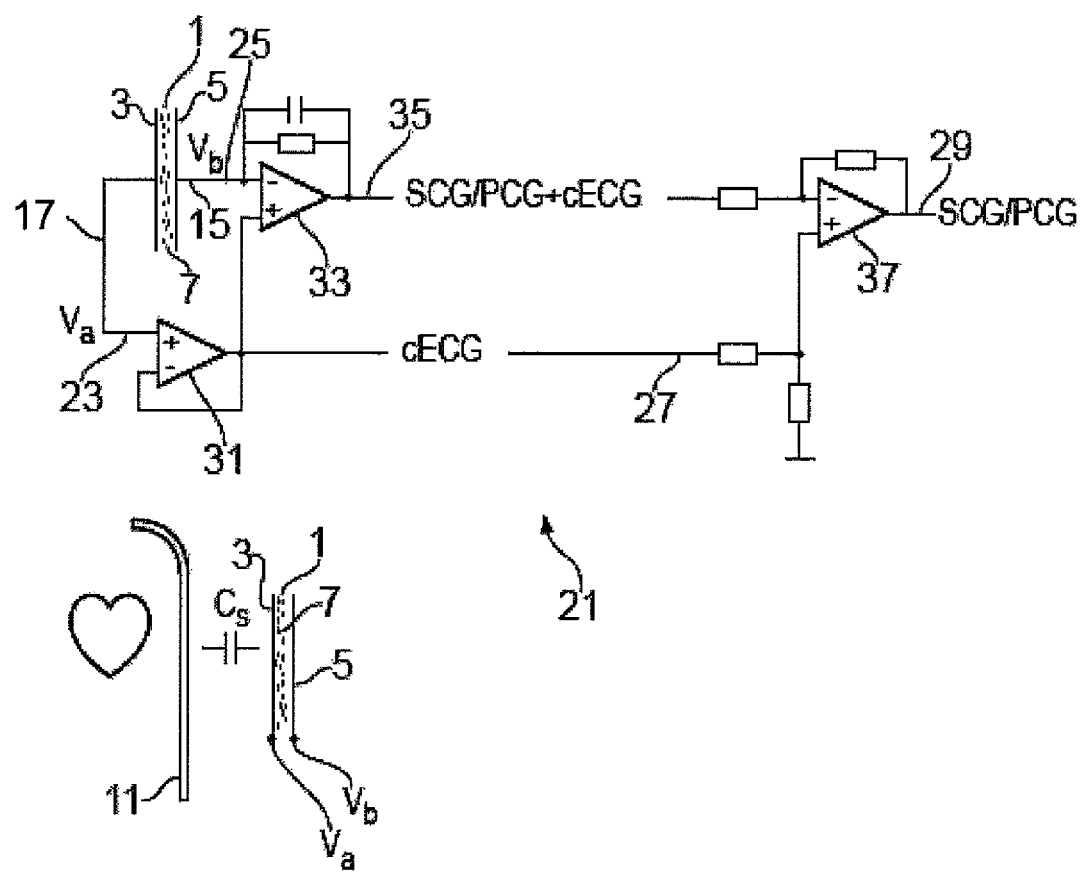

For a better understanding of various examples that are useful for understanding the detailed description, reference will now be made by way of example only to the accompanying drawings in which:

FIG. 1 illustrates an example apparatus;
FIG. 2 illustrates example electronic circuitry;
FIG. 3 illustrates an example apparatus and electronic circuitry; and
FIGS. 4A to 4D illustrate another example apparatus and electronic circuitry.

DETAILED DESCRIPTION

The figures show apparatus 1 and electronic circuitry 21 for sensing different types of biosignals. The apparatus 1 comprises at least a first electrode 3 and a second electrode 5 which are arranged to sense both bioelectric and biomechanical signals. The electronic circuitry 21 is arranged to receive input signals from the apparatus 1 and provide output signals indicative of both the bioelectric and biomechanical signals.

The apparatus 1 and electronic circuitry 21 therefore provide means for measuring both a bioelectric signal and a biomechanical signal. The same sensing apparatus 1 is used to transduce both the bioelectric signal and a biomechanical signal into electrical output signals. This enables the biomechanical measurements to be made at the same location, or very similar locations, to the biomechanical measurements. In some examples this could enable biomechanical measurements to be made at exactly the same location as the bioelectrical measurements. This enables more information about the health and/or physical state of the subject 11 to be obtained. This may also improve the accuracy and/or reliability of the information that is obtained.

In the following description the term coupled means operationally coupled. Any number or combination of intervening elements can exist between coupled components, including no intervening elements.

FIG. 1 schematically illustrates an apparatus 1 according to examples of the disclosure. The apparatus 1 may be for sensing biosignals. The apparatus 1 enables biosignals 13 from a subject 11 to be transduced into electrical output signals 15, 17. In examples of the disclosure the apparatus 1 enables both bioelectric signals and biomechanical signals to be transduced into electrical output signals 15, 17. Therefore the apparatus 1 provides a single sensing device that may be arranged to detect both bioelectrical and biomechanical signals simultaneously.

The apparatus 1 comprises; a first electrode 3 arranged to enable an output 17 indicative of a bioelectrical signal to be provided; a second electrode 5; and a deformable material 7 positioned between the first electrode 3 and the second electrode 5 wherein the deformable material 7 is arranged to cause a change in charge distribution across the first electrode 3 and second electrode 5 in response to deformation of the deformable material 7 to enable an output 15 indicative of a biomechanical signal to be provided by the apparatus 1.

The apparatus 1 is arranged to be positioned on the body of a subject 11. A subject could be a person or an animal. A subject could be a patient who may be undergoing diagnostic tests or any other health monitoring applications. In some examples of the disclosure the apparatus 1 may be provided within a small wearable pad, or other device, which may be arranged to be attached to the subject's body so that the apparatus 1 can detect biosignals 13 generated by the subject 11. The apparatus 1 may be arranged to be adhered or otherwise secured to the subject's body. When the apparatus 1 is secured to the subject's body the electrodes 3, 5 may be positioned adjacent to the subject's skin. In some examples this may enable the subject 11 to move but ensure that the apparatus 1 remains fixed in position on the subject's body. The apparatus 1 may be arranged to be positioned on any suitable part of the subject's body, such as the torso, limbs, head or any other location.

The first electrode 3 comprises means for detecting a bioelectric signal and providing an electrical output 17 indicative of the detected bioelectrical signal. In some examples the first electrode 3 could be a capacitive coupling electrode which may be arranged to detect charge displacements caused by bioelectric signals of the subject 11. In such examples the apparatus 1 is arranged so that the first electrode 3 is not positioned in direct contact with the subject 11 when the apparatus 1 is in use. In such examples the apparatus 1 may comprise an insulating material which may be positioned overlaying the first electrode 3 so that when the apparatus 1 is in use the insulating material is positioned between the first electrode 3 and the subject 11.

In other examples the apparatus 1 may be arranged so that first electrode 3 can be positioned in galvanic contact with the subject 11 so as to provide a direct current path between the subject 11 and the first electrode 3. In such examples a conductive gel, or other material, may be used to facilitate the detection of the bioelectric signals. The conductive gel, or other material, may be coated on the skin of the subject 11 and/or on the surface of the first electrode 3 to improve the conductive path between the first electrode 3 and the subject 11.

The bioelectrical signal that is sensed by the first electrode 3 may comprise any time varying electrical signal that is generated by the subject's body. The bioelectrical signal may comprise an autonomic signal. The autonomic signal may be controlled subconsciously by the subject 11. In some examples the bioelectrical signals may comprise electrical signals that are generated within the subject's body by the subject's heartbeat. In some examples the bioelectrical signals could comprise electrical activity of the subject's brain or other parts of their nervous system. The bioelectrical signal could comprise at least one of an electrocardiogram signal, electroencephalogram signal, electromyogram signal, electrooculogram signal, electrogastrogram signal, galvanic skin potential or any other suitable bioelectrical signal.

The second electrode 5 is positioned within the apparatus 1 so that the first electrode 3 overlays the second electrode 5. The second electrode 5 may be arranged to provide a guard for the first electrode 3. The apparatus 1 may be coupled to electronic circuitry 21 which is arranged so that the second electrode 5 provides a guard for the first electrode 3. The second electrode 5 may be driven to a guard voltage to reduce current leakage from the first electrode 3. The second electrode 5 may guard the first electrode 3 from electronic circuitry 21 which may be coupled to the apparatus 1 and/or other environmental factors which may affect the output 15 provided by the first electrode 3.

In examples of the disclosure a layer of deformable material 7 is provided between the first electrode 3 and the second electrode 5. The deformable material 7 is arranged within the apparatus 1 so that the deformable material 7 is deformed when the subject's body moves or changes shape. For example, the deformable material 7 may change shape in response to biomechanical signals such as vibrations within the subject's body caused by the subject's heartbeat.

The biomechanical signals that cause the deformation of the deformable material 7 may comprise any time varying mechanical signal that is generated by the subject's body. The biomechanical signal may comprise an autonomic signal. The autonomic signal may be controlled subconsciously by the subject 11. In some examples the biomechanical signals may comprise mechanical signals that are generated within the subject's body by the subject's heartbeat, respiration, abdominal sounds or other body movements. In some examples the biomechanical signal 15 could comprise at least one of ballistocardiogram signal, seismocardiogram signal, phonocardiogram signal or any other suitable signal.

In examples of the disclosure other parts of the apparatus 1 may also be deformable in addition to the deformable material 7. This may enable the deformable material 7 to change shape in response to a biomechanical signal. For example, in embodiments where the first electrode 3 is positioned adjacent to the subject 11, the first electrode 3 may be flexible so that both the first electrode 3 and the deformable material 7 change shape in response to biomechanical signals. When the apparatus 1 is coupled to a subject's body both the first electrode 3 and the deformable material 7 may be deformed in response to the biomechanical signals. Similarly, in embodiments where the second electrode 5 is positioned adjacent to the subject 11, the second electrode 5 may be flexible. In some examples both the first electrode 3 and the second electrode 5 could be flexible.

In examples of the disclosure the deformable material 7 comprises a material in which the charged particles within the material are rearranged in response to deformation of the material. The rearrangement of the charged particles may comprise a change in the distribution of the particles within the deformable material 7. For instance, the deformable material 7 may comprise at least one of; ferroelectret film, piezoelectric film or any other suitable material. The deformable material 7 may be positioned within the apparatus such that deformation of the deformable material 7 causes a change in charge distribution across the first electrode 3 and second electrode 5 when it is deformed.

The deformable material 7 is positioned between the first electrode 3 and the second electrode 5 so that the first electrode 3, second electrode 5 and deformable material 7 form a capacitor. The charge on the second electrode 5 is determined by both the voltage at the first electrode 3 and the deformation of the deformable material 7. As the deformation of the deformable material 7 is caused by a biomechanical signal the second electrode 5 provides an electrical output signal 15 which contains information indicative of the biomechanical signal. The output signal 15 provided by the second electrode 5 also comprises a component which is dependent upon the voltage at the first electrode 3. As this is affected by the bioelectrical signals, the electrical output signal 15 also comprises a component which is dependent upon the bioelectrical signal.

The apparatus 1 could be coupled to electronic circuitry 21 so that the output signal 15 can be measured by the electronic circuitry 21. The electronic circuitry 21 may also be arranged to separate the biomechanical signal from other components within the output signal 15. Examples of electronic circuitry 21 which could be used are shown in FIGS. 2 to 4.

FIG. 2 schematically illustrates electronic circuitry 21 according to examples of the disclosure. The electronic circuitry 21 could be coupled to an apparatus 1 as described above. In some examples the electronic circuitry 21 may be provided within the same device as the sensing apparatus 1. For instance, both the electronic circuitry 21 and the sensing apparatus 1 may be provided within a wearable pad, or other device, that could be attached to the subject 11. In other examples some parts of the electronic circuitry 21 could be located remote to the sensing apparatus 1. In such cases there may be a wireless communication link provided between the sensing apparatus 1 and some of the components of the electronic circuitry 21.

In examples of the disclosure the electronic circuitry 21 comprises: a first input 23 arranged to receive a first input signal from a sensing apparatus 1; a second input 25 arranged to receive a second input signal from the sensing apparatus 1; means 24 for processing the first input signal and the second input signal so as to enable a biomechanical signal to be separated from a bioelectrical signal; wherein the means 24 for processing the first input signal and the second input signal is coupled to a first output 27 arranged to provide an output indicative of the bioelectric signal coupled to a second output 29 arranged to provide an output indicative of the biomechanical signal.

The electronic circuitry 21 may be arranged so that the first input signal is received from the first electrode 3 of the sensing apparatus 1. The first input signal therefore comprises information indicative of the bioelectrical signal. The first input 23 may be coupled to the first output 27. The first input 23 may be coupled to the first output 27 via the processing means 24 so that the first output 27 provides a signal indicative of the bioelectrical signal. In some examples the first input 23 processing means 24 may comprise a non-inverting amplifier or any other suitable means.

The electronic circuitry 21 may also be arranged so that the second input signal is received from the second electrode 5 of the sensing apparatus 1. The second input signal therefore comprises components indicative of the biomechanical signal. It is to be appreciated that the second input signal may also comprise other components in addition to the components indicative of the biomechanical signal. The second input 25 may be coupled to the second output 29. The second input 25 may be coupled to the second output 29 via the processing means 24 so that the second output provides a signal indicative of the biomechanical signal. The processing means 24 may comprise circuitry that is arranged to separate the biomechanical signal from the other components of the input signal so that the second output 29 provides a signal indicative of the biomechanical signal. In some examples the processing means 24 may comprise a charge amplifier or any other suitable means. In some examples the processing means 24 may also comprise a difference amplifier, or any other suitable means. The difference amplifier may be arranged to separate the biomechanical signal from the other components of the input signal.

In some examples the electronic circuitry 21 may be arranged to enable the second electrode 5 to provide an electrical guard for the first electrode. In some examples the electronic circuitry 21 may be arranged to provide a guard voltage to the second electrode 5 of the apparatus 1.

FIG. 3 illustrates an example apparatus 1 and electronic circuitry 21 coupled to the apparatus 1 according to an example of the disclosure. The apparatus 1 comprises a first electrode 3, second electrode 5 and deformable material 7 as described above. The electronic circuitry 21 comprises a first input 23, second input 25, first output 27 and second output 29 as described above. The example apparatus 1 and electronic circuitry 21 may be provided within a wearable sensing device which is arranged to sense the subject's biosignals.

The example apparatus 1 of FIG. 3 is arranged so that when the apparatus 1 is in use the first electrode 3 is positioned between the second electrode 5 and the subject's body. In some examples the first electrode 3 could be in galvanic contact with the subject's body so that a direct current path is provided between the first electrode 3 and the subject's body. In other examples the first electrode 3 could form a capacitive sensor so that an insulating layer may be provided between the first electrode 3 and the subject's body.

In the example of FIG. 3 the bioelectric signals that the apparatus 1 is arranged to sense comprise electrocardiogram (ECG) signals and the biomechanical signals that the apparatus 1 is arranged to sense comprise seismocardiogram (SCG) signals and/or phonocardiogram (PCG) signals. The apparatus 1 may be arranged so that it can be positioned on the subject's body at suitable locations to enable the ECG, SCG and PCG signals to be detected. For example the apparatus 1 may be provided in a small contact pad, or other suitable device, which can be adhered to the subject's torso or limbs. It is to be appreciated that the apparatus 1 could be used to sense other types of biosignals in other examples of the disclosure.

The first output signal 17, having a voltage $V_a$, provided by the first electrode 3 is provided to the first input 23 of the electronic circuitry 21. In the example of FIG. 3 the first input 23 is coupled to a non-inverting amplifier 31. In the example of FIG. 3 the non-inverting amplifier is a voltage follower. Other types of non-inverting amplifiers may be used in other examples of the disclosure.

The non-inverting amplifier 31 provides the first output 27 of the electronic circuitry 21 which is indicative of the bioelectrical signal.

The second output signal 15 provided by the second electrode 5 is provided to the second input 25 of the electronic circuitry 21. In the example of FIG. 3 the second input 25 is coupled to an inverting amplifier 33. In the example of FIG. 3 the inverting amplifier 33 is a charge amplifier which is arranged to integrate the charge from the second electrode 5.

In the example of FIG. 3 the output 15 from the second electrode and at a voltage $V_b$ is provided to the negative input of the charge amplifier 33. The output from the non-inverting amplifier 31 is provided to the positive input. This enables the second electrode 5 to act as a guard for the first electrode 3.

The charge amplifier 33 provides an output 35 which has a first component indicative of the biomechanical signal and a second component indicative of the bioelectrical signal. The output 35 of the charge amplifier 33 is provided to a difference amplifier 37. The difference amplifier 37 is arranged to provide the second output 29 of the electronic circuitry 21. The output from the charge amplifier 33 is provided to the negative terminal of the difference amplifier 37 and the output of the non-inverting amplifier 31 is provided to the positive terminal so that the output 29 of the difference amplifier 37 is indicative of the biomechanical signal. The difference amplifier 37 may remove the bioelectrical components from the signal. The difference amplifier 37 may remove other components such as the guard voltage from the input signal.

Therefore the example apparatus 1 and electronic circuitry 21 of FIG. 3 enable a single sensing apparatus 1 to detect both bioelectrical and biomechanical signals. The electronic circuitry 21 enables two different outputs to be provided indicative of each of these signals.

FIGS. 4A to 4D illustrate another example apparatus 1 and electronic circuitry 21 according to examples of the disclosure. The apparatus 1 comprises a first electrode 3, second electrode 5 and deformable material 7 which may be as described above. In the examples of FIGS. 4A to 4D the apparatus 1 also comprises a conductive shield 41.

The conductive shield 41 may comprise means for shielding the first electrode 3. In some examples the conductive shield 41 may be arranged to shield the first electrode 3 from triboelectric charges. The conductive shield 41 may comprise any suitable material.

FIG. 4A illustrates a plan view of an example first electrode 3 and a conductive shield 41. The first electrode 3 and the conductive shield 41 may be arranged on the same layer within the apparatus 1 so that the first electrode 3 covers a portion of the surface and the conductive shield 41 covers a different portion of the surface.

In the example of FIG. 4A the conductive shield 41 and the first electrode 3 have interdigitated structures. The interdigitated structures provide discontinuities in the surface of the first electrode 3. The interdigitated structures comprise a plurality of extended projections 45, 43. The first electrode 3 comprises a first plurality of extended projections 43 and the conductive shield 41 comprises a second plurality of extended projections 45. The conductive shield 41 and the first electrode 3 are arranged so that the extended projections 45 of the conductive shield 5 are positioned between the extended projections 43 of the first electrode 3. The extended projections 45 of the conductive shield 5 are separate from the extended projections 43 of the electrode 3 so that there is no direct current path between the conductive shield 41 and the first electrode 3.

It is to be appreciated that other arrangements of the conductive shield 41 and the first electrode 3 could be used in other examples of the disclosure. FIG. 4B illustrates a plan view of another example arrangement in which the conductive shield 41 comprises a hemisphere and the first electrode 3 also comprises a hemisphere. Other shapes and arrangements could be used in other embodiments.

In some examples the conductive shield 41 and the first electrode 3 may provide the outer surface of the apparatus 1 so that, in use, the conductive shield 41 and the first electrode 3 contact the subject's body. In other examples an insulating layer may be provided overlaying, at least a portion of the conductive shield 41 and the first electrode 3 so that, in use, the insulating layer contacts the subject's body. The insulating material could comprise any suitable material. In some examples the insulating material may comprise a fabric. The fabric could comprise a material which, like human skin, has a tendency to charge positively such as nylon. In other examples the insulating material could comprise a solder mask.

In some examples the insulating layer might cover the entire of the conductive shield 41 and the first electrode 3. In other examples the first insulating layer 31 may partially cover the conductive shield 41 and the electrode 3. For instance, the insulating layer could cover the first electrode 3 but may leave the conductive shield 41 uncovered.

FIG. 4C illustrates a plan view of the second electrode 5 which may be provided within the apparatus 1. The second electrode 5 may comprise a continuous conductive surface which acts as a guard between the first electrode 3 and the circuitry 21.

FIG. 4D illustrates the example apparatus 1 coupled to electronic circuitry 21. As described above the first output signal 17 provided by the first electrode 3 is provided to the first input 23 of the electronic circuitry 21. In the example of FIG. 4D the first input is coupled to a non-inverting amplifier 31 which may be a voltage follower or other suitable type of non-inverting amplifier. The non-inverting amplifier 31 provides the first output 27 of the electronic circuitry 21 which is indicative of the bioelectrical signal.

The output of the non-inverting amplifier 31 may also be provided to the conductive shield 41. This enables the conductive shield 41 to be driven to the same potential as the first electrode 3. In some examples a buffer 47 may be provided between the non-inverting amplifier 31 and the conductive shield 41.

The second output signal 15 provided by the second electrode 5 is provided to the second input 25 of the electronic circuitry 21. In the example of FIG. 4D the second input 25 is coupled through an input impedance $Z_i$ to an inverting amplifier 33 which is arranged to integrate the charge from the second electrode 5. There is a feedback impedance $Z_f$ in parallel with the inverting amplifier 33.

In the example of FIG. 4D the output 15 from the second electrode is provided to the negative input of the charge amplifier 33. The output from the non-inverting amplifier 31 is provided to the positive input. This enables the second electrode 5 to act as a guard for the first electrode 3. The output 35 from the charge amplifier 33 may be provided to a difference amplifier 37 which is not shown in FIG. 4D.

The example of FIG. 4D therefore provides another apparatus 1 and corresponding circuitry which enables a single sensing apparatus 1 to detect both bioelectrical and biomechanical signals.

In the examples described above the apparatus 1 and electronic circuitry 21 may be provided as part of a system which can be used to measure ECG signals or any other suitable types of signals. In such systems a plurality of sensing apparatus 1 and corresponding electronic circuitry 21 may be provided. The plurality of sensing apparatus 1 may be arranged to be located on different parts of the subject's body. For instance, if the apparatus 1 are being used to obtain ECG signals the apparatus 1 could be located across the chest of the subject and on the respective arms and legs. In other examples the apparatus 1 may be arranged to be located on other parts of the subject's body. For instance, where the bioelectrical signal comprises an electrooculogram signal the apparatus 1 may be arranged to be positioned around a subject's eyes.

In examples of the disclosure the same sensing apparatus 1 transduces both a biomechanical signal and a bioelectric signal. This enables more information to be obtained from the subject 11 with a single sensing device. This also enables the bioelectric signal and the biomechanical signal to be measured simultaneously and at the same location on the subject's body. This may enable accurate information about the subject's bio signals to be obtained.

For example, where the apparatus 1 is used to obtain ECG and SCG/PCG signals the information from these signals can be combined to measure cardiac time intervals such as the pre-ejection period (PEP) and the left ventricular ejection time (LVET). It is to be appreciated that other parameters of the subject's health or wellbeing could be measured using apparatus 1 and electronic circuitry according to examples of the disclosure.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:
1. A system comprising:
an apparatus comprising:
a first electrode arranged to detect charge displacements caused by a bioelectrical signal of a subject;
an output of the first electrode to carry a signal indicative of the detected charge displacements caused by the bioelectrical signal;
a second electrode;
an output of the second electrode; and
a deformable material positioned between the first electrode and the second electrode such that deformation of the deformable material by the subject causes a change in charge distribution across the first electrode and second electrode;
wherein the deformable material is formed in a layer contacting the first electrode on a first side of the deformable material and contacting the second electrode on a second side of the deformable material, the second side is opposite from the first side, and wherein the first electrode is a single electrode that completely overlays a side of the second electrode that contacts the deformable material;
wherein the first electrode, the second electrode, the output of the second electrode, and the deformable material are configured to allow a charge to be created on the second electrode determined by both a voltage at the first electrode and the deformation of the deformable material and to enable the output of the second electrode to carry a signal having a first component, formed at least from the change in charge distribution caused by the deformation and being indicative of a biomechanical signal corresponding to the deformation, and having a second component, formed at least based on the voltage at the first electrode and being indicative of the bioelectrical signal; and
electronic circuitry comprising:
a first input connected to the output of the first electrode;
a second input connected to the output of the second electrode;
a first amplifier having an input connected to the first input and another input connected to the output of the first amplifier and configured to process a first input signal on the first input and configured to produce an output having the bioelectrical signal;

a second amplifier being a difference amplifier;

a third amplifier having an input coupled to the second input and another input coupled to the output of the first amplifier, the third amplifier configured to integrate charge from the second input;

wherein the difference amplifier has an input coupled to the output of the third amplifier and another input coupled to the output of the first amplifier and is configured to process a second input signal on the output of the third amplifier via taking at least a difference between the first input signal and the second input signal so as to enable the biomechanical signal to be separated from the bioelectrical signal;

a first output coupled to an output of the first amplifier to provide an output indicative of the bioelectrical signal; and a second output coupled to an output of the difference amplifier and arranged to provide an output indicative of the biomechanical signal.

2. An apparatus as claimed in claim 1, wherein the first electrode is a capacitive coupling electrode arranged to form the bioelectrical signal.

3. An apparatus as in claim 1, wherein the second electrode is coupled to the first electrode and the electronic circuitry is arranged so that the second electrode is biased to the voltage of the first electrode.

4. An apparatus as claimed in claim 1 wherein the third amplifier is arranged to provide a guard voltage to the second electrode to at least guard the first electrode at least from the first, second, and third amplifiers and associated circuitry, and wherein the difference amplifier is arranged to remove the guard voltage from a signal on the output of the third amplifier.

5. An apparatus as claimed in claim 4, wherein the first amplifier is a non-inverting amplifier, and wherein the output of the non-inverting amplifier is provided as a reference input to the third amplifier and to another input of the difference amplifier, wherein the first and second electrodes and the third amplifier are configured so that outputs of the first and second electrodes are referenced to each other.

6. An apparatus as claims in claim 4, wherein the second electrode has a continuous conductive surface that is positioned to act as a guard between the first electrode and the electronic circuitry.

* * * * *